(12) United States Patent
Shelly et al.

(10) Patent No.: US 9,526,854 B2
(45) Date of Patent: Dec. 27, 2016

(54) INDUCTANCE COMPENSATION IN A PRESSURE SUPPORT SYSTEM

(75) Inventors: Benjamin Irwin Shelly, Pittsburgh, PA (US); Pooja Chatterjee, Jersey City, NJ (US); Peter Douglas Hill, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 637 days.

(21) Appl. No.: 13/697,383

(22) PCT Filed: Apr. 26, 2011

(86) PCT No.: PCT/IB2011/051814
§ 371 (c)(1),
(2), (4) Date: Nov. 12, 2012

(87) PCT Pub. No.: WO2011/141845
PCT Pub. Date: Nov. 17, 2011

(65) Prior Publication Data
US 2013/0056006 A1    Mar. 7, 2013

Related U.S. Application Data

(60) Provisional application No. 61/333,291, filed on May 11, 2010.

(51) Int. Cl.
*F16K 31/02* (2006.01)
*A61M 16/00* (2006.01)

(52) U.S. Cl.
CPC .. *A61M 16/0051* (2013.01); *A61M 2016/0027* (2013.01); *A61M 2016/0039* (2013.01)

(58) Field of Classification Search
None
See application file for complete search history.

(56) References Cited

U.S. PATENT DOCUMENTS

| 4,448,192 A | | 5/1984 | Stawitcke | |
|---|---|---|---|---|
| 4,561,287 A | * | 12/1985 | Rowland | 95/11 |
| 4,788,974 A | * | 12/1988 | Phuc | 128/204.21 |

(Continued)

FOREIGN PATENT DOCUMENTS

| CN | 1432416 A | 7/2003 |
|---|---|---|
| CN | 101365507 A | 2/2009 |

(Continued)

*Primary Examiner* — Bradley Philips
*Assistant Examiner* — Eric Bryant
(74) *Attorney, Agent, or Firm* — Michael W. Haas

(57) ABSTRACT

A system and method for delivering a flow of gas to an airway of a patient (54). The system includes a gas flow generator (52) and a patient circuit (56) comprising a conduit (100) that communicates the flow of gas to a patient. A sensor (62) is configured to measure a rate of the flow gas and generate flow signals based on the measured rate of flow. A controller (64) is operatively connected with the gas flow generator (52) and the sensor (62) and is configured to control a pressure of the flow of gas provided to the patient. The controller (64) receives the flow signals from the sensor (62), determines a rate of change in the flow of the gas, and modifies or compensates the pressure of the flow of gas provided to the patient if the rate of change in the flow of gas provided to the patient exceeds a threshold amount.

16 Claims, 4 Drawing Sheets

(56) References Cited

U.S. PATENT DOCUMENTS

| | | | |
|---|---|---|---|
| 5,107,830 A * | 4/1992 | Younes | A61M 16/00 128/204.18 |
| 5,303,700 A | 4/1994 | Weismann | |
| 5,632,269 A * | 5/1997 | Zdrojkowski | A61M 16/0051 128/204.21 |
| 5,865,173 A | 2/1999 | Froehlich | |
| 6,142,150 A | 11/2000 | O'Mahoney | |
| 6,427,689 B1 | 8/2002 | Estes | |
| 7,040,321 B2 | 5/2006 | Gobel | |
| 7,972,414 B2 * | 7/2011 | Aylsworth et al. | 95/8 |
| 2002/0020410 A1 * | 2/2002 | Rydin et al. | 128/200.24 |
| 2006/0213511 A1 | 9/2006 | Hansen | |
| 2007/0044799 A1 * | 3/2007 | Hete | A61M 16/10 128/205.11 |
| 2007/0157930 A1 | 7/2007 | Soliman | |
| 2008/0236585 A1 * | 10/2008 | Parker | A61M 16/0078 128/205.23 |
| 2008/0308101 A1 * | 12/2008 | Spandorfer | A61M 15/009 128/203.14 |
| 2009/0038617 A1 * | 2/2009 | Berthon-Jones | A61M 16/00 128/204.23 |

FOREIGN PATENT DOCUMENTS

| | | |
|---|---|---|
| GB | 2294400 A | 1/1996 |
| JP | 2004511311 A | 4/2004 |
| JP | 05184676 A | 7/2005 |
| JP | 2009511221 A | 3/2009 |
| RU | 2357762 C1 | 6/2009 |

* cited by examiner

INDUCTANCE COMPENSATION IN A PRESSURE SUPPORT SYSTEM

CROSS-REFERENCE TO RELATED APPLICATIONS

This patent application claims the priority benefit under 35 U.S.C. §371 of international patent application no. PCT/IB2011/051814, filed Apr. 26, 2011, which claims the priority benefit under 35 U.S.C. §119(e) of U.S. Provisional Application No. 61/333,291 filed on May 11, 2010, the contents of which are herein incorporated by reference.

BACKGROUND OF THE INVENTION

1. Field of the Disclosure

The present invention relates generally to a method and apparatus for providing pressure compensation for a pressure drop due to dynamic flow in a pressure support system.

2. Description of the Related Art

Positive pressure ventilatory modes of operation are commonly used in devices that provide respiratory assistance, such as continuous positive airway pressure (CPAP) devices. The positive pressure devices are typically programmed by a physician to provide a specified pressure and often different inspiratory and expiratory pressures. Alternatively, the positive pressure devices can be used in a volume control mode, in which a physician programs the volume to be delivered on a given breath.

In order to provide the prescribed pressure or volume, the pressure device typically measures pressure and flow near the outlet of the device and then estimates the pressure and volume that is being provided to the airways of the patient. The patient circuit tubing has characteristics that affect the pressure and flow delivered to the patient. The device typically estimates such effects on the pressure and flow to provide the proper amount of pressure.

Compensation for patient tubing is known to those skilled in the art. For example, there are devices that compensate for the flow resistance of the patient circuit tubing, such as using "automatic tube compensation," where the pressure drop over the patient circuit is estimated to be proportional to the square of the flow rate and a proportionality constant is defined by the user input. There are also devices that compensate for the shortfall of the volume delivered to the patient due to pneumatic compliance.

The amount of pressure drop over the patient circuit is estimated so that an accurate or proper amount of pressure may be provided to the patient. Regulatory standards require positive pressure devices to meet certain accuracy standards under dynamic flow conditions. While typical pressure support devices may be able to provide pressure at a level that is sufficiently comfortable for the patient and can meet regulatory requirements without compensating for the pressure drop due to dynamic flow, the tubing typically used heretofore has been of a relatively large diameter. If smaller diameter tubing were to be used, the pressure drop due to the dynamic flow in the smaller tubing would cause the pressure support systems to have more undesirable pressure "swings." Consequently, the pressure provided to the patient may be less comfortable and may be unable to meet regulatory standards.

For example, the inductance of air in a tube, L, is defined as:

$$L = \frac{\rho_{air} \cdot l_{tube}}{A_{tube} \cdot g}, \quad \text{Eq. 1.1}$$

where:
L is the inductance of the tube in $cmH_2O/(liters/sec^2)$,
$\rho_{air}$ is the density of the air, grams/liter,
$l_{tube}$ is the length of the tube in cm,
$A_{tube}$ is the cross-sectional area of the tube, $cm^2$, and
g is the gravitational constant, 981 $cm/sec^2$.

Therefore, a nominal inductance value might be 0.0775 $cmH_2O/(liters/sec^2)$ for a standard-sized tube having a length of 6 ft. and an internal diameter of 22 mm used for non-invasive pressure therapy. During normal respiration, the total pressure swing caused by the inductive effect may only be on the order of 0.2-0.3 $cmH_2O$, peak to peak. This small, transient error is often not enough for the patient to detect. If the diameter of a six foot tubing were to be as small as 15 mm, 11 mm, or perhaps even smaller, problems may result. For example, in the case of 11 mm tubing, the inductance value may be as high as 0.310 $cmH_2O/(liters/sec^2)$, and the peak-to-peak pressure error could be up to 1.2 $cmH_2O$, which could cause discomfort to the patient.

Accordingly, it is an object of the present invention to provide a pressure support system that overcomes the shortcomings of conventional pressure support system. This object is achieved according to one embodiment of the present invention by providing a pressure support system t for delivering a flow of gas to an airway of a patient that include a gas flow generator that generates a flow of gas and a patient circuit. The patient circuit is coupled to the gas flow generator and comprises a conduit adapted to communicate the flow of gas to an airway of a patient. The system also includes a sensor associated with the gas flow generator and/or the patient circuit and is configured to measure the flow of gas in the patient circuit and generate flow signals based on the measured flow. The system further includes a controller operatively connected with the gas flow generator and the sensor. The controller is configured to control a pressure of the flow of gas provided to the patient. The controller receives the flow signals from the sensor and determines a rate of change in the flow of the gas provided to the patient. The controller modifies or compensates the pressure of the flow of gas provided to the patient if the rate of change in the flow of gas provided to the patient exceeds a threshold amount.

SUMMARY OF THE INVENTION

Another aspect provides a method of ventilating or delivering a flow of gas to a patient. The method includes delivering a flow of gas to the airway of a patient from a source of gas via a patient circuit. The patient circuit comprises a conduit adapted to communicate the flow of gas to the airway of the patient. The method further includes measuring the flow of gas and generating flow signals based upon the measure of flow. The method also includes controlling a pressure of the flow of gas provided to the patient by 1) receiving the flow signals and determining a rate of change in the flow of the gas provided to the patient and 2) modifying or compensating the pressure of the flow of gas provided to the patient if the rate of change in the flow of gas provided to the patient exceeds a threshold amount.

Another aspect provides a system for ventilating a patient. The system includes means for delivering a flow of gas to the airway of a patient from a source of gas via a patient circuit. The patient circuit includes a conduit adapted to communicate the flow of gas to the airway of the patient. The system also includes means for measuring a rate of the flow and generating flow signals based upon the measured flow of gas in the patient circuit. The system further includes means for controlling a pressure of the flow of gas provided to the patient by 1) receiving the flow signals and determining a rate of change in the flow of the gas provided to the patient and 2) modifying or compensating the pressure of the flow of gas provided to the patient if the rate of change in the flow of gas provided to the patient exceeds a threshold amount.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein can be considered drawn to scale. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
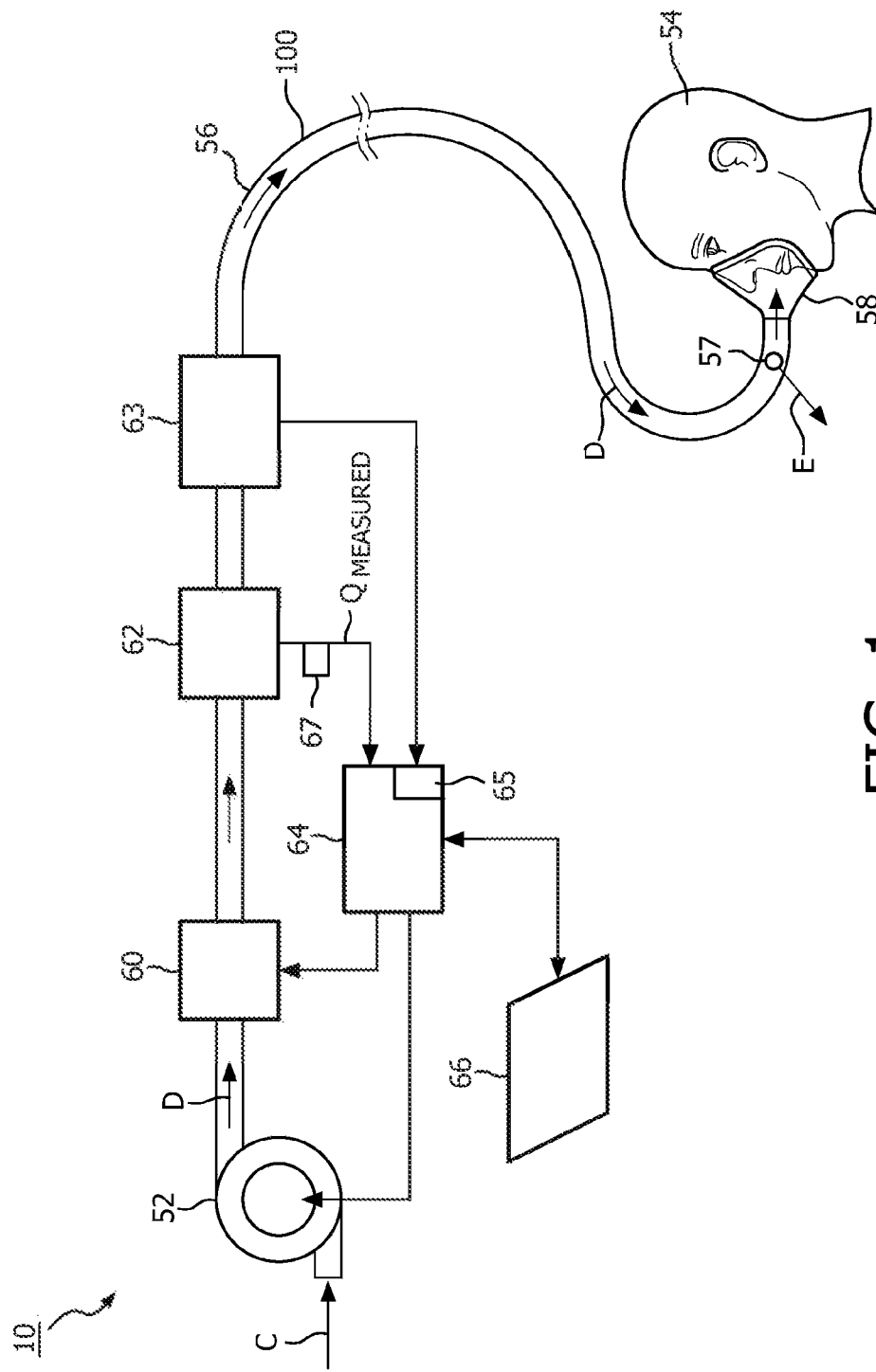
FIG. 1 is a functional block diagram of a positive airway pressure support system adapted to implement the pressure support therapy according to the principles of the present invention.

FIG. 1 schematically illustrates an airway pressure support system 10 suitable for providing an improved variable positive airway pressure mode of pressure support to a patient according to the principles of the present invention. The pressurized flow of gas, generally indicated by arrow D from a gas flow/pressure generator 52 is delivered, via a delivery conduit 56 to a breathing mask or patient interface 58 of any known construction, which is typically worn by or otherwise attached to a patient 54 to communicate the flow of gas to the airway of the patient. Delivery conduit 56 is also commonly referred to as a patient circuit. In some embodiments, delivery conduit 56 may comprise a flexible tubing 100. In some embodiments, tubing 100 of the patient circuit has a diameter of 15 mm or less.

As mentioned above, tubing 100 has characteristics that may affect the pressure and flow of the gas provided to the patient. For example, the tubing may cause flow resistance and inductance that affects the pressure or flow of the gas provided to the patient. To provide the proper amount of pressure or flow of gas to the patient, system 10 compensates for the pressure drop in the patient circuit resulting from the dynamic gas flow. Pressure support system 10 modifies or compensates the pressure of the flow of gas provided to the patient based on the effects of the patient tubing. In particular, the pressure support system determines a rate of change in the flow of the gas provided to the patient and modifies or compensates the pressure of the flow of gas provided to the patient if the rate of change in the flow of gas provided to the patient exceeds a threshold amount.

Figure 2A:
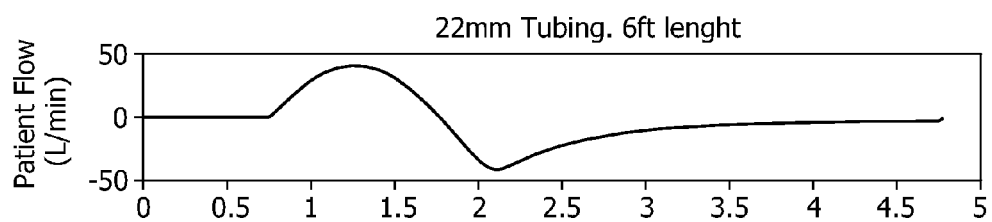
FIGS. 2A-2D are waveforms of the flow, the pressure drop, the flow differential, and estimated error in pressure drop for a patient circuit tubing in accordance with an embodiment.
Figure 2B:
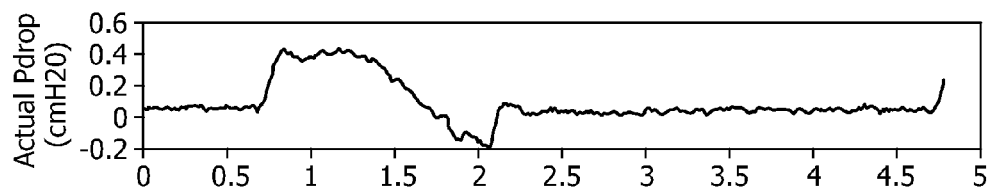
Figure 2C:
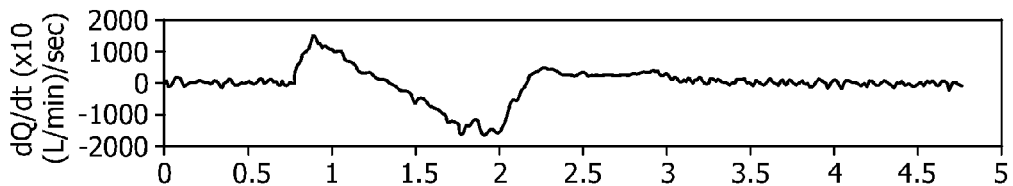
Figure 2D:
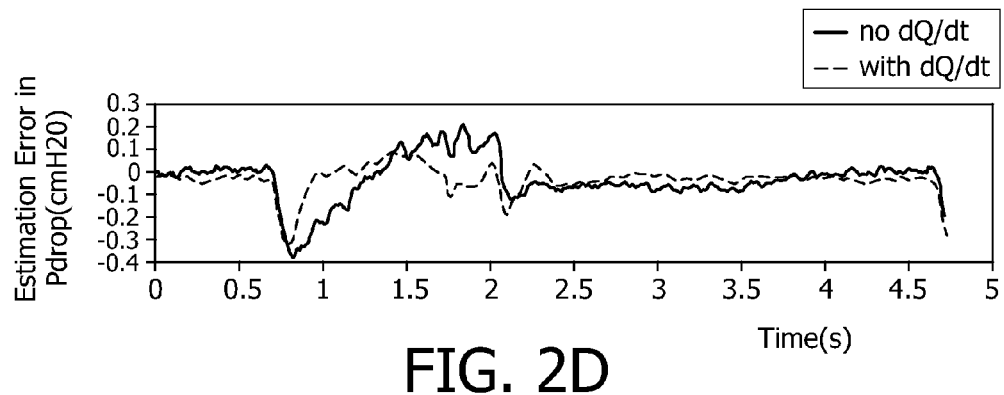
Figure 3A:
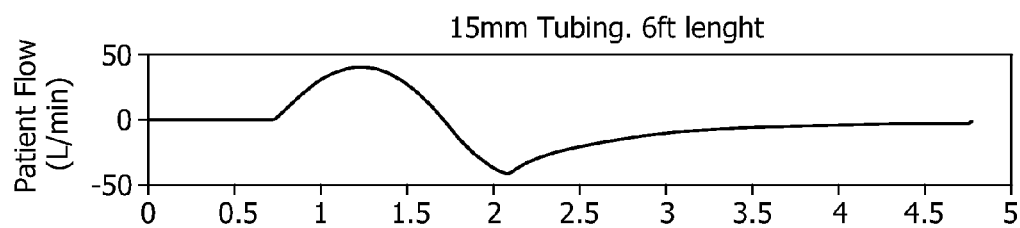
FIGS. 3A-3D are waveforms of the flow, the pressure drop, the flow differential, and estimated error in pressure drop for a patient circuit tubing in accordance with an embodiment.
Figure 3B:
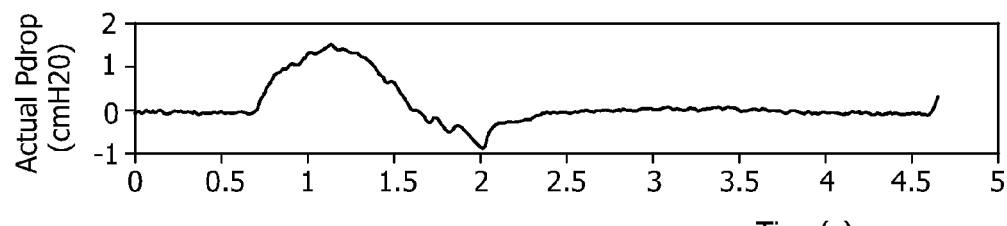
Figure 3C:
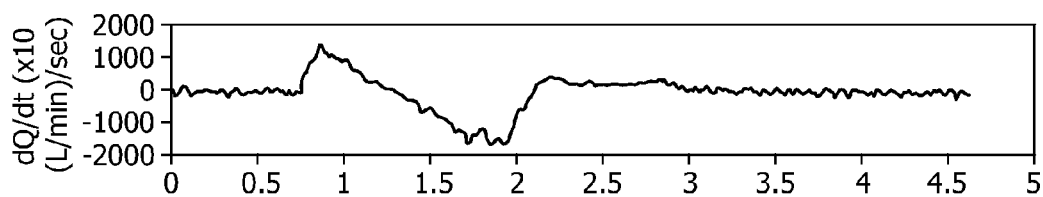
Figure 3D:
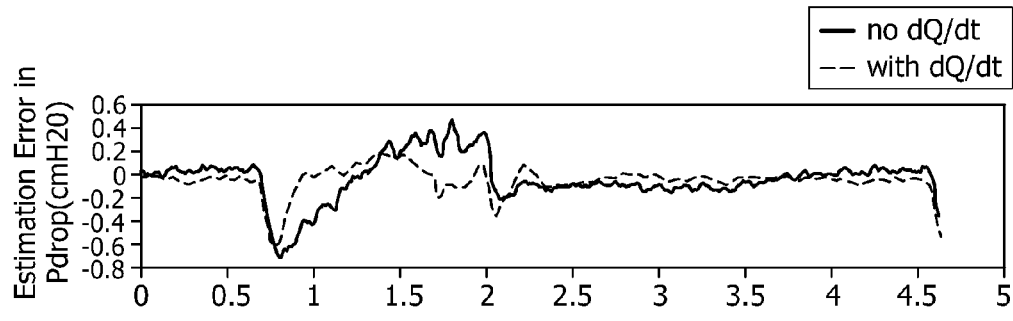

FIGS. 2A-2D show exemplary waveforms of the patient flow, pressure drop, flow differential, and estimation error in the pressure drop for patient tubing 100 that is 22 mm in diameter and 6 ft. in length. In contrast, FIGS. 3A-3D show exemplary waveforms of the patient flow, pressure drop, flow differential, and estimation error in the pressure drop for patient tubing 100 that is 15 mm in diameter and 6 ft. in length. As shown in FIGS. 2A and 2D and FIGS. 3A and 3D, the estimation error in pressure drop without compensating for the inductive pressure drop spikes at the beginning of inhalation and as the flow decreases from inhalation to exhalation. As shown in FIGS. 2D and 3D, the estimation error in pressure drop without compensating for the inductive effect is greater in patient tubing 100 having a diameter of 15 mm (see FIG. 3D) than in the patient tubing having a diameter of 22 mm (see FIG. 2D). Thus, system 10 can compensate for the inductive effect of the dynamic flow. This may be used for tubing of any diameter or length, but may have particular benefit for tubing with smaller diameter or greater lengths (where more inductance is experienced).

Referring back to FIG. 1, pressure support system 10 includes a gas flow/pressure generator 52, such as a blower used in a conventional CPAP or bi-level pressure support device, piston, bellows, compressor, or any other device that receives gas, generally indicated by arrow C, from any suitable source, e.g., a pressurized tank of oxygen or air, the ambient atmosphere, or a combination thereof. Gas flow/pressure generator 52 generates a flow of gas, such as air, oxygen, or a mixture thereof, for delivery to an airway of a patient 54 at relatively higher and lower pressures.

System 10 may be configured to generate the pressurized flow of breathable gas according to one or more modes. A non-limiting example of one such mode is Continuous Positive Airway Pressure (CPAP). CPAP has been used for many years and has proven to be helpful in promoting regular breathing. Another mode of pressure support therapy is bi-level therapy. In a bi-level positive air pressure mode, two or more levels of positive air pressure are supplied to a patient. The present invention further contemplates providing an auto-titration continuous or bi-level therapy in which the pressure changes based on a monitored variable, such as whether the patient is experiencing an apnea.

In an embodiment, positive airway pressure support system 10 essentially functions as a bi-level pressure support system, and, therefore, includes all of the capabilities necessary in such systems in order to provide separate IPAP and EPAP levels to the patient. This includes receiving the necessary parameters via input commands, signals, instructions or information for providing a bi-level pressure, such as maximum and minimum IPAP and EPAP settings. A flow signal $Q_{measured}$ from a flow sensor 62 is also provided to the pressure support process, which controls the pressure controller to output the desired inspiratory and expiratory waveforms. Typically, carrying out the pressure support operation includes estimating or determining the actual patient flow $Q_{patient}$ based on the flow signal $Q_{measured}$, determining whether the patient is in the inspiratory or expiratory phase of the respiratory cycle and providing an I/E state signal indicative of the respiratory state of the patient, and triggering and cycling the pressure support system.

Pressure support system 10 shown in FIG. 1 is a single-limb system, meaning that the patient circuit includes only a delivery conduit 56 connecting the patient to the pressure support device. As such, an exhaust vent 57 is provided in the delivery conduit for venting exhaled gasses from the system as indicated by arrow E. It should be noted that the exhaust vent can be provided at other locations in addition to or instead of in the delivery conduit, such as in the patient interface device. It should also be understood that the exhaust vent can have a wide variety of configurations depending on the desired manner in which gas is to be vented from the pressure support system.

The present invention also contemplates that the variable positive airway pressure support system can be a two-limb system, having a delivery conduit and an exhaust conduit connected to the patient.

In the illustrated exemplary embodiment, patient interface 58 is a nasal/oral mask. It is to be understood, however, that patient interface 58 can include a nasal mask, nasal pillows, tracheal tube, endotracheal tube, or any other device that provides the gas flow communicating function. Also, for purposes of the present invention, the phrase "patient interface" can include delivery conduit 56 and any other structures that connect the source of pressurized gas to the patient.

The various components may be provided in or coupled to the patient circuit. For example, a bacteria filter, pressure control valve, flow control valve, sensor, meter, pressure filter, humidifier and/or heater can be provided in or attached to the patient circuit. Likewise, other components, such as muffler and filters can be provided at the inlet of gas flow/pressure generator 52 and at the outlet of valve 60.

In the illustrated embodiment, variable positive airway pressure support system 10 includes a pressure controller in the form of a valve 60 provided in delivery conduit 56. Valve 60 controls the pressure of the flow of gas from gas flow/pressure generator 52 delivered to the patient. For present purposes, gas flow/pressure generator 52 and valve 60 are collectively referred to as a "pressure generating system" because they act in concert to control the pressure and/or flow of gas delivered to the patient.

It should be apparent that other techniques for controlling the pressure delivered to the patient by the gas flow/pressure generator, such as varying the blower speed, either alone or in combination with a pressure control valve, are contemplated by the present invention. Thus, valve 60 is optional depending on the technique used to control the pressure of the flow of gas delivered to the patient. If valve 60 is eliminated, the pressure generating system corresponds to gas flow/pressure generator 52 alone, and the pressure of gas in the patient circuit is controlled, for example, by controlling the motor speed of the gas flow/pressure generator.

Pressure support system 10 further includes a flow sensor 62 that measures the flow of gas within delivery conduit 56. In accordance with an embodiment shown in FIG. 1, flow sensor 62 is interposed in line with delivery conduit 56, such as downstream of valve 60. Pressure support system 10 may also include a pressure sensor 63 for measuring the pressure of gas delivered from the system. As shown in FIG. 1, pressure sensor 63 may also be interposed in line with delivery conduit 56, such as downstream of valve 60. However, it is contemplated that sensors 62, 63 may located at any suitable location in system 10. In some embodiments, pressure sensor 34 is located at or proximate a gas outlet. Pressure sensor 63 may be positioned to measure the pressure of gas flow entering conduit 56.

Other techniques for measuring the patient flow of the patient are contemplated by the present invention. It is contemplated that flow may be measured at other locations along delivery conduit 56. Also, it is know to measure the pressure and/or flow by monitoring the operation of flow/pressure generator 52.

A user interface 66 is provided for setting various parameters used by the pressure support system 10, as well as for displaying and outputting information and data to a user, such as a clinician or caregiver. This enables data, results, and/or instructions and any other communicable items, collectively referred to as "information," to be communicated between the patient and system 10. Examples of interface devices suitable for inclusion in user interface 66 include a keypad, buttons, switches, a keyboard, knobs, levers, a display screen, a touch screen, speakers, a microphone, an indicator light, an audible alarm, a printer, and/or other interface devices. In one embodiment, user interface 66 includes a plurality of separate interfaces. In one embodiment, user interface 66 includes at least one interface that is provided integrally with the housing containing the components of the pressure support system. It is also contemplated that input/output terminals may be provided so that the operation information and data collected by the pressure support system can be monitored and controlled remotely.

Controller 64 may be a processor or microprocessor that is capable of implementing and executing routines for monitoring characteristics of patient respiration and controlling the flow of gas based thereon as discussed in detail below. As such, the controller may include one or more of a digital processor, an analog processor, a digital circuit designed to process information, an analog circuit designed to process information, a state machine, and/or other mechanisms for electronically processing information. In addition, controller 64 includes memory 65, or memory arrays for storing and buffering information necessary to implement the techniques discussed herein. It is to be understood, that controller 64 can be a single processing component, or can be comprised of multiple components (memories, processor, arrays, logic circuits, etc.) operating in conjunction to implement the techniques discussed herein. Controller 64 may be configured to implement process 400, shown in FIG. 4 and which will be described in detail later, by software; hardware; firmware; some combination of software, hardware, and/or firmware; and/or other mechanisms for configuring processing capabilities on processor 24.

In an embodiment, controller 64 controls gas flow/pressure generator 52, valve 60, or both to deliver a pressure waveform to an airway of patient 54. In an exemplary embodiment of the present invention, the pressure waveform is essentially a bi-level pressure waveform that alternates between an IPAP level and an EPAP level. In some embodiments, the IPAP level is variable under the direction of controller 64 as discussed below. The maximum and minimum IPAP levels ($IPAP_{max}$, $IPAP_{min}$) are provided to the controller via input device 66 from a user. Alternatively or additionally, the EPAP level is variable under the direction of controller 64. In such embodiments, the maximum and minimum IPAP levels ($EPAP_{max}$, $EPAP_{min}$) are provided to the controller via input device 66 from a user. It should be understood that the maximum and minimum IPAP/EPAP levels can also be pre-established and stored in the controller as a default or in lieu of input parameters from the system operator. Controller 64 may include storage arrays and buffers to calculate parameters in real-time, and store the results in moving windows.

Controller 64 may determine the amount of pressure to be provided to the patient during inspiration. The controller may determine the total pressure drop due to the resistive and inductive effects of patient tubing 100. The total pressure drop is then added to the pressure provided to the patient during the next patient inspiration.

Figure 4:
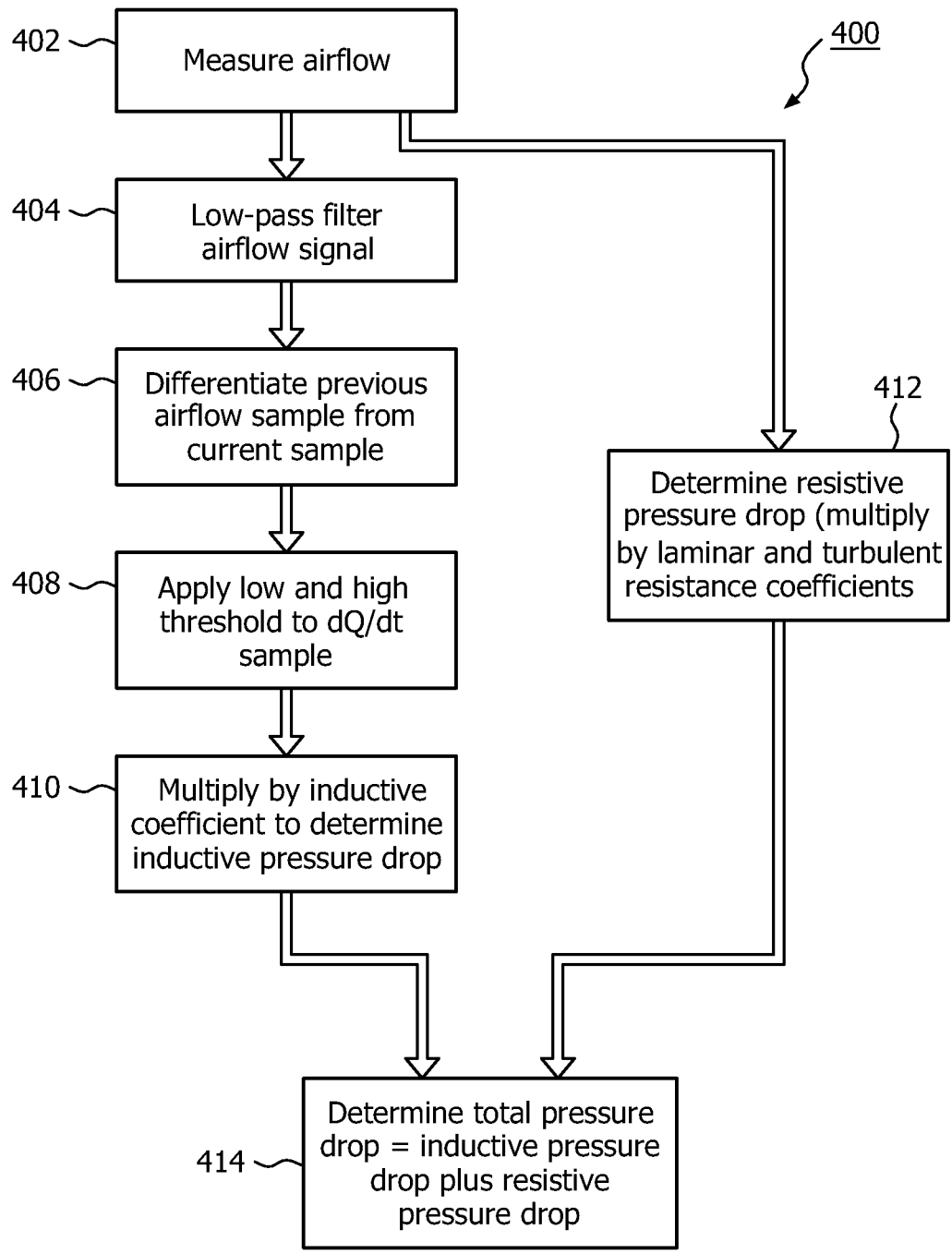
FIG. 4 is a flowchart illustrating a portion of the process for implementing the pressure support mode of the present invention.

FIG. 4 is a flowchart showing the process or algorithm 400 that the system 10 uses in some embodiments to compensate for the effects of the patient circuit tubing 100. In step 402, the system 10 obtains the output of flow sensor 62. In some embodiments, the output is sampled at a sampling rate, such as 100 samples/second. Process 400 then proceeds to step 404 and 412.

In step 404, the flow signals obtained in step 402 may be filtered using a filter 67 to reduce or remove noise in the flow signals. Filtering of the flow signals may be required enable the system 10 to provide more accurate pressure compensation. Filter 67 may be one or a combination of a low pass filter, a high-pass filter, or band-pass filter. In some embodiments, filter 67 may include a data storage capability to store a history of flow signals.

In some embodiments, the flow signals may be passed through a low pass filter which attenuates high frequency noise and produces a clean total air flow signal on an output. The resulting output from the filters may be a patient flow signal with reduced noise.

Process 400 then proceeds to step 406. In step 406, system 10 differentiates the previous sample from the current sample to obtain the differential flow or the rate of change of the flow. A high-pass filter may be used in this step 406. In one embodiment, steps 404 and 406 may be performed using a band pass filter. The comparison may optionally be made in controller 64. The differential flow values may be stored in memory 65, or any other storage device. The flow values reflective of the filtered flow signals may also be stored in memory 65, or any other storage device.

In step 408, the differential flow obtained in step 406 is compared with a low threshold and a high threshold. This comparison may be implemented in controller 64. System 10 may optionally include an AD converter to convert the flow signals for processing by the controller 64. In some embodiments, a threshold may be used to "condition" the differential flow value. The flow signals and the differential flow signals may still be noisy even though the signals have been filtered. However, adding more filters may cause delay. Thus, the threshold(s) may be used to prevent the system from providing spurious amounts of pressure compensation and without the added delay.

In step 408, process 400 determines whether to compensate using the differential flow value based on whether the differential flow value is above a low threshold and/or is below a high threshold. In some embodiments, the low threshold may be, just for example, 30 (L/min)/sec. In some embodiments, the high threshold may be, just for example, 200 (L/min)/sec. Alternatively or additionally, the differential flow signals may be additionally filtered. If the differential flow value exceeds the low threshold and is below the high threshold, process 400 proceeds to step 410. In some embodiments, if the differential flow is below the low threshold, process 400 may proceed to step 414 and the differential flow is set to zero so that the total pressure drop may be determined using only the resistive pressure drop.

If the differential flow is above the high threshold, process 400 may proceed to step 414 and the differential flow is set to the high threshold value so that the total pressure drop is a function of the high threshold value. The absolute value of the differential flow may be used when comparing the differential flow to the threshold values. In addition, the low threshold and high threshold values may be positive and negative. For example, in one embodiment having a low threshold of 30 (L/min)/sec, if the differential flow is between −30 (L/min)/sec and 30 (L/min)/sec, the differential flow is set to 0. In one embodiment, if the differential flow is lower than −200 (L/min)/sec (the high threshold value), the differential flow is set to −200 (L/min)/sec.

In step 410, the controller 64 multiplies the differential flow value obtained in step 408 by an inductive coefficient. The coefficient C may be defined as a function of the diameter of tubing 100, the length of the tubing 100, and the density of the gas. In some embodiments, the value of the coefficient C may be set by the user. C may be stored in memory 65, or in any other storage device.

In step 412, the system 10 determines the resistive pressure drop. The resistive pressure drop may be determined using known methods, such as according to the following equation:

$$P_{drop} = A \cdot Q^2 + B \cdot Q, \qquad \text{Eq. 1.2}$$

where A is a turbulent resistance coefficient, B is a laminar resistance coefficient, and Q is defined as the rate of flow. The coefficients A and B may be defined by the user input. Alternatively, it is also possible to automatically determine the A and B constants using a pressure sensor proximal to the patient. In some embodiments, the coefficients A, B, and C may be determined empirically for a given patient tubing 100 or may be determined based on pressure feedback. In some embodiments, calibration tests may be performed to determine the values of A, B, and C. The values of A, B, and C may be stored in memory 65, RFID (radio frequency identification) devices, or other storage devices.

In step 414, the system 10 calculates and compensates for the total pressure drop over the patient circuit tubing that is due to the dynamic flow, e.g. the pressure drop due to the changing flow. In this step, the controller 64 adds the value of the inductive pressure drop obtained in step 410 to the value of the resistive pressure drop obtained in step 412. Therefore, the pressure drop over the tubing may be estimated as:

$$P_{drop} = A \cdot Q^2 + B \cdot Q + C \cdot \frac{\partial Q}{\partial t}, \qquad \text{Eq. 1.3}$$

where A is the turbulent resistance coefficient, B is the laminar resistance coefficient, and C is the inductive coefficient, Q is defined as the rate of flow, and ∂Q/∂t is an approximation of the rate of change of the flow, or also known as the flow differential.

Controller 64 may use Equation 1.3 during pressure compensation to compensate for the pressure drop due to the resistive effect and inductive effect of the dynamic flow through the tubing 100. Controller 64 may provide pressure compensation based on the calculated pressure drop in step 414 at the beginning of inspiration.

In some embodiments, fixed values may be used for the flow differentials instead of or in addition to differentiating the flow signals as described above. For example, in some embodiments, the system 10 determines when the flow rate is increasing and provides a fixed value for the flow differential during pressure compensation. System 10 may also determine when the flow rate is decreasing and provide another fixed value for the flow differential during pressure compensation. If system 10 determines that the flow rate is relatively stable, the system 10 may provide a third fixed value for the flow differential during pressure compensation. The fixed values may be set by the user or may be determined by the system. Although the amount of pressure compensation provided may not be as accurate as using the flow differential obtained via process 400, using fixed values may still be effective to compensate for the inductive pressure drop due to dynamic flow.

The flow differential, as determined using the algorithm shown in FIG. 4, may also be used to compensate for the delay in the sensing system and control system of the pressure support system 10. The flow sensor may have an inherent delay and signal conditioning. The electronics processing the signal from the flow sensor may add further delay. Thus, this delay may cause errors in the estimation of the pressure drop over the circuit. Some of these errors may be removed by providing compensation using the differential flow value obtained as described above.

Controller 64 may use the total pressure drop value calculated in step 414 when providing the prescribed pressure to the patient. The measured pressure may be reduced by the total pressure drop to estimate the actual pressure that is being provided to the patient.

Controller 64 may determine whether it is in the inspiratory phase of the respiratory cycle. This may be accomplished using any conventional technique for differentiating between inspiration and expiration. In an embodiment, a flag is set whenever the patient is in inspiration.

In embodiments where a flag is set during inspiration, if the patient is in the inspiratory phase of the respiratory cycle, controller 64 causes the gas flow/pressure generator to begin to deliver the inspiratory pressure to the patient that compensates for the total pressure drop calculated in step 414 of process 400. The controller may then control the pressure delivered to the patient during or within the respiratory cycle. The controller determines whether the pressure support delivered to the patient is sufficient. The system may continuously implement the process 400 to ensure that a proper and accurate amount of pressure is being provided to the patient. In some embodiments, the process may be implemented at different times within a single inspiration or expiration phase so that the rate of change of the flow of the gas can be calculated in a single breathing cycle.

Embodiments of the invention, such as the controller, microprocessors, or processors, for example, may be made in hardware, firmware, software, or various combinations thereof. The invention may also be implemented as instructions stored on a machine-readable medium, which may be read and executed using one or more processing devices. In one embodiment, the machine-readable medium may include various mechanisms for storing and/or transmitting information in a form that may be read by a machine (e.g., a computing device). For example, a machine-readable storage medium may include read only memory, random access memory, magnetic disk storage media, optical storage media, flash memory devices, and other media for storing information, and a machine-readable transmission media may include forms of propagated signals, including carrier waves, infrared signals, digital signals, and other media for transmitting information. While firmware, software, routines, or instructions may be described in the above disclosure in terms of specific exemplary aspects and embodiments performing certain actions, it will be apparent that such descriptions are merely for the sake of convenience and that such actions in fact result from computing devices, processing devices, processors, controllers, or other devices or machines executing the firmware, software, routines, or instructions.

It can be appreciated that the embodiments are not to be limited to the specific time periods, percentages, and constants noted above. Rather, other values for these quantities can be used so long as the general principles of the present invention are maintained. In addition, these quantities need not be fixed. Instead, they can be dynamically altered by the controller 64 based on the monitored condition of the patient. This can be done, for example, to treat the patient more aggressively if they are not responding to the current treatment scheme, and vise versa.

Although the invention has been described in detail for the purpose of illustration based on what is currently considered to be the most practical embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for delivering a flow of gas to an airway of a patient, the system comprising:
   a gas flow generator that generates a flow of gas;
   a patient circuit coupled to the gas flow generator and comprising a conduit adapted to communicate the flow of gas to an airway of a patient;
   a sensor associated with the gas flow generator and/or the patient circuit and configured to measure a rate of the flow of the gas and generate flow signals based on the measured rate of flow; and
   a controller operatively connected with the gas flow generator and the sensor, the controller configured to control a pressure of the flow of gas provided to the patient, wherein the controller receives the flow signals from the sensor and determines a rate of change in the flow rate of the gas provided to the patient, and wherein the controller compensates the pressure of the flow of gas provided to the patient based upon;
   (a) a resistive pressure drop in the patient circuit,
   (b) whether the rate of change in the flow rate of as provided to the patient is within a threshold range, wherein, responsive to the rate of change in the flow rate being within the threshold range, the controller:
     multiplies the rate of change in the flow rate by an inductive coefficient to determine an inductive pressure drop,
     determines a total pressure drop based on the inductive pressure drop and the resistive pressure drop, and
     compensates the pressure of the flow of as based on the total pressure drop.

2. The system of claim 1, further comprising a filter that receives the flow signals from the sensor and is configured to filter the signals for processing by the controller.

3. The system of claim 2, wherein the filter is a low pass filter, a high pass filter, or a band pass filter.

4. The system of claim 1, wherein the conduit comprises a tube having a diameter less than 15 mm.

5. The system of claim 1, wherein determining the rate of change of the gas flow rate comprises determining a difference between a current flow rate value and a previous flow rate value.

6. The system of claim 1, wherein the inductive coefficient is a function of a diameter of the tube, gas density, and tube length.

7. The system of claim 1, wherein, responsive to the rate of change in the flow rate being below the low threshold amount, the controller determines the total pressure drop based on the resistive pressure drop and compensates the pressure of the flow of gas based on the total pressure drop.

8. A method of providing a flow of gas, comprising:
  delivering a flow of gas from a source of gas via a patient circuit, the patient circuit comprising a conduit adapted to communicate the flow of gas;
  measuring a rate of the flow of gas and generating flow signals based upon the measured rate of flow; and
  controlling a pressure of the flow of gas by (1) receiving the flow signals and determining a rate of change in the flow rate of the gas, and (2) compensating the pressure of the flow of gas based upon: (a) a resistive pressure drop in the patient circuit, (b) whether the rate of change in the flow rate of gas is within a threshold range, wherein, responsive to the rate of change in the flow rate being within the threshold range,
    the rate of change in the flow rate is multiplied by an inductive coefficient to determine an inductive pressure drop,
    a total pressure drop is determined based on the inductive pressure drop and the resistive pressure drop, and
    the pressure of the flow of gas is compensated based on the total pressure drop.

9. The method of claim 8, further comprising filtering the signals for processing with a controller.

10. The method of claim 8, wherein the filtering is performed by a low pass filter, a high pass filter, or a band pass filter.

11. The method of claim 8, further comprising differentiating flow rate values reflective of the flow signals to determine the rate of change in the flow rate of gas.

12. The method of claim 8, wherein the inductive coefficient is a function of a diameter of the tube, gas density, and tube length.

13. The method of claim 8, wherein determining the rate of change of the gas flow rate comprises determining a difference between a current flow rate value and a previous flow rate value.

14. The method of claim 8, wherein, responsive to the rate of change in the flow rate being below the low threshold amount, the total pressure drop is determined based on the resistive pressure drop and the pressure of the flow of gas is compensated based on the total pressure drop.

15. A system for ventilating a patient, comprising:
  means for delivering a flow of gas to the airway of a patient from a source of gas via a patient circuit, the patient circuit comprising a conduit adapted to communicate the flow of gas to the airway of the patient;
  means for measuring a rate of the flow of gas and generating flow signals based upon the measure of rate of flow, and
  means for controlling a pressure of the flow of gas provided to the patient by
    1) receiving the flow signals and determining a rate of change in the flow rate of gas, and
    2) compensating the pressure of the flow of gas provided to the patient as based upon (a) a resistive pressure drop in the patient circuit, (b) whether the rate of change of the flow rate of gas provided to the patient is within a threshold range, wherein, responsive to the rate of change in the flow rate being within the threshold range:
      multiplies the rate of change in the flow rate by an inductive coefficient to determine an inductive pressure drop,
      determines a total pressure drop based on the inductive pressure drop and the resistive pressure drop, and
      compensates the pressure of the flow of gas based on the total pressure drop.

16. The system of claim 15, wherein, responsive to the rate of change in the flow rate being below the low threshold amount, the means for controlling determines the total pressure drop based on the resistive pressure drop and compensates the pressure of the flow of gas based on the total pressure drop.

* * * * *